(12) United States Patent
Ichiki et al.

(10) Patent No.: US 10,113,948 B2
(45) Date of Patent: Oct. 30, 2018

(54) PARTICLE DETECTION METHOD, PARTICLE DETECTION DEVICE AND PARTICLE DETECTION SYSTEM

(71) Applicants: The University of Tokyo, Tokyo (JP); NIKON CORPORATION, Tokyo (JP)

(72) Inventors: Takanori Ichiki, Tokyo (JP); Kuno Suzuki, Iruma-gun (JP); Daishi Tanaka, Konosu (JP); Jiro Inoue, Yokohama (JP); Kazuya Ota, Tokyo (JP)

(73) Assignees: The University of Tokyo, Tokyo (JP); Nikon Corporation, Tokyo (JP)

( * ) Notice: Subject to any disclaimer, the term of this patent is extended or adjusted under 35 U.S.C. 154(b) by 0 days.

(21) Appl. No.: 15/490,727

(22) Filed: Apr. 18, 2017

(65) Prior Publication Data

US 2017/0219477 A1 Aug. 3, 2017

Related U.S. Application Data

(63) Continuation of application No. PCT/JP2015/079699, filed on Oct. 21, 2015.

(30) Foreign Application Priority Data

Oct. 24, 2014 (JP) .................................. 2014-217807

(51) Int. Cl.
*G01N 15/14* (2006.01)
*B01L 3/00* (2006.01)
*G01N 21/53* (2006.01)
*C12M 1/34* (2006.01)
*G01N 15/00* (2006.01)
*G01N 15/10* (2006.01)

(52) U.S. Cl.
CPC ...... *G01N 15/1463* (2013.01); *B01L 3/50273* (2013.01); *B01L 3/502715* (2013.01);
(Continued)

(58) Field of Classification Search
CPC .............. G02B 26/001; G02B 26/0841; G02B 6/0036; G02B 26/08; G02B 26/0833;
(Continued)

(56) References Cited

U.S. PATENT DOCUMENTS

| 5,370,842 A | 12/1994 | Miyazaki et al. |
| 2002/0040851 A1 | 4/2002 | McNeil-Watson et al. |

(Continued)

FOREIGN PATENT DOCUMENTS

| EP | 0 545 284 | 6/1993 |
| EP | 1 154 266 | 11/2001 |

(Continued)

OTHER PUBLICATIONS

International Search Report and Written Opinion dated Dec. 22, 2015 in International Patent Application No. PCT/JP2015/079699, 18 pages.

*Primary Examiner* — Michael P Stafira
(74) *Attorney, Agent, or Firm* — Squire Patton Boggs (US) LLP

(57) ABSTRACT

A particle detection method in which particles in a sample are detected includes: a mounting step of mounting, on a stage portion, a fluid device including a channel through which the particles can move; an irradiation step of irradiating the channel with illumination light; and a detection step of detecting scattered light generated from the particles by irradiation with the illumination light. In the irradiation step, the illumination light is converged such as to enter the channel by passing through, among side surfaces of the channel, only the first side surface that faces an illumination light incident direction.

21 Claims, 7 Drawing Sheets

(52) U.S. Cl.
CPC ....... B01L 3/502761 (2013.01); C12M 41/36 (2013.01); G01N 15/1484 (2013.01); G01N 21/53 (2013.01); B01L 2200/025 (2013.01); B01L 2200/0647 (2013.01); B01L 2300/0654 (2013.01); B01L 2300/0887 (2013.01); B01L 2300/168 (2013.01); B01L 2400/0421 (2013.01); G01N 2015/0038 (2013.01); G01N 2015/0065 (2013.01); G01N 2015/1075 (2013.01); G01N 2015/1493 (2013.01); G01N 2201/06113 (2013.01)

(58) Field of Classification Search
CPC .. G02B 3/0056; G02B 5/0252; G02B 6/0083; G02B 1/12; G02B 26/007; G02B 26/02; G02B 3/0037; G02B 5/001; G02B 5/021; G02B 5/02
See application file for complete search history.

(56) References Cited

U.S. PATENT DOCUMENTS

| | | |
|---|---|---|
| 2005/0140971 A1 | 6/2005 | Yamaguchi et al. |
| 2006/0197034 A1 | 9/2006 | Shirai et al. |
| 2007/0252983 A1* | 11/2007 | Tong .................. G01J 3/26 356/301 |
| 2010/0110177 A1 | 5/2010 | Yamada et al. |
| 2011/0000285 A1* | 1/2011 | Biggs ................. G01N 11/16 73/54.41 |
| 2014/0027286 A1 | 1/2014 | Ikegami et al. |
| 2014/0219870 A1 | 8/2014 | Ryu |
| 2015/0049333 A1* | 2/2015 | Gourley ............. G01N 15/1484 356/338 |
| 2015/0168400 A1 | 6/2015 | Ichiki et al. |

FOREIGN PATENT DOCUMENTS

| | | |
|---|---|---|
| EP | 1 489 403 | 12/2004 |
| EP | 2 889 623 | 7/2015 |
| JP | 05-240872 | 9/1993 |
| JP | 2002-005888 | 1/2002 |
| JP | 2003-279471 | 10/2003 |
| JP | 2006-276000 | 10/2006 |
| JP | 2008-261740 | 10/2008 |
| JP | 2014-521110 | 8/2014 |
| WO | WO 2012/147426 | 11/2012 |
| WO | WO 2013/014407 | 1/2013 |
| WO | WO 2014/030590 | 2/2014 |

* cited by examiner

PARTICLE DETECTION METHOD, PARTICLE DETECTION DEVICE AND PARTICLE DETECTION SYSTEM

CROSS-REFERENCE(S) TO RELATED APPLICATION(S)

The present application is a Continuation Application of International Application PCT/JP2015/079699, filed on Oct. 21, 2015, which claims priority based on Japanese Patent Application No. 2014-217807, filed on Oct. 24, 2014. The contents of the above-mentioned applications are incorporated herein by reference.

BACKGROUND

Field of the Invention

The present invention relates to a particle detection method, a particle detection device and a particle detection system.

Background

Technologies for capturing images of particles moving through a medium by means of microscope observation, and measuring the number or speed of movement of the particles based on the captured image information are known. For example, JP 2002-5888A discloses a measurement apparatus including electrodes provided at both ends of a flow path inside a capillary cell, a laser that emits a laser beam, and a detection device that detects scattered light generated by laser irradiation. This measurement apparatus measures the speed of movement of particles or the like by detecting the scattered light generated by laser irradiation of a medium through which particles move due to the application of electricity to the electrodes.

SUMMARY

In order to improve the particle detection limit, it is important to reduce the noise contained in the signal obtained by detecting the scattered light. However, the measurement apparatus described in JP 2002-5888A also detects scattered light generated by the laser beam impinging on the side walls facing the flow path. The intensity of the scattered light generated at the side walls is several orders of magnitude greater than the intensity of the scattered light from the particles being observed, so there is a possibility that the scattered light generated by the side walls will create noise, leading to a decrease in the accuracy of detection of the particles being observed.

According to an embodiment, the present invention provides a particle detection method in which particles in a sample are detected, comprising: a mounting step of mounting, on a stage portion, a fluid device comprising a channel through which the particles can move; an irradiation step of irradiating the channel with illumination light; and a detection step of detecting scattered light generated from the particles by irradiation with the illumination light, wherein in the irradiation step, the illumination light is converged such as to enter the channel by passing through, among side surfaces of the channel, only the first side surface that faces an illumination light incident direction.

According to an embodiment, the present invention provides a particle detection device in which particles in a sample are detected, the particle detection device comprising: a stage portion on which is to be mounted a fluid device including a channel into which a sample containing particles can be introduced; an irradiation portion configured to irradiate the channel with illumination light; an adjustment portion configured to adjust the illumination light; and a detection portion configured to detect scattered light generated from the particles in the sample by irradiation with the illumination light, wherein the adjustment portion adjusts the convergence angle of the illumination light such that an irradiation region on a first side surface of the channel that faces an illumination light incident direction is focused within the first side surface.

According to an embodiment, the present invention provides a particle detection system comprising: a fluid device that includes a channel into which a sample containing particles can be introduced; and the particle detection device according to the second embodiment of the present invention.

DETAILED DESCRIPTION OF THE INVENTION

Hereinafter, embodiments of a particle detection method and a particle detection device of the present invention will be described with reference to FIGS. 1 to 10.

Figure 1:
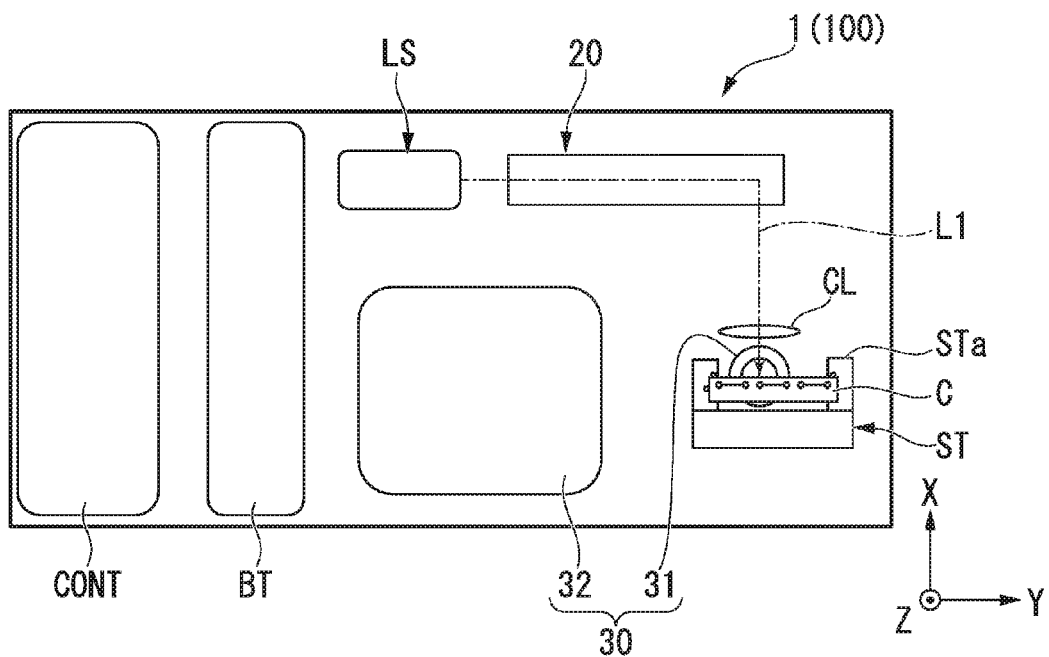
FIG. 1 is a schematic plan view of a particle detection device according to an embodiment of the present invention.
Figure 2:
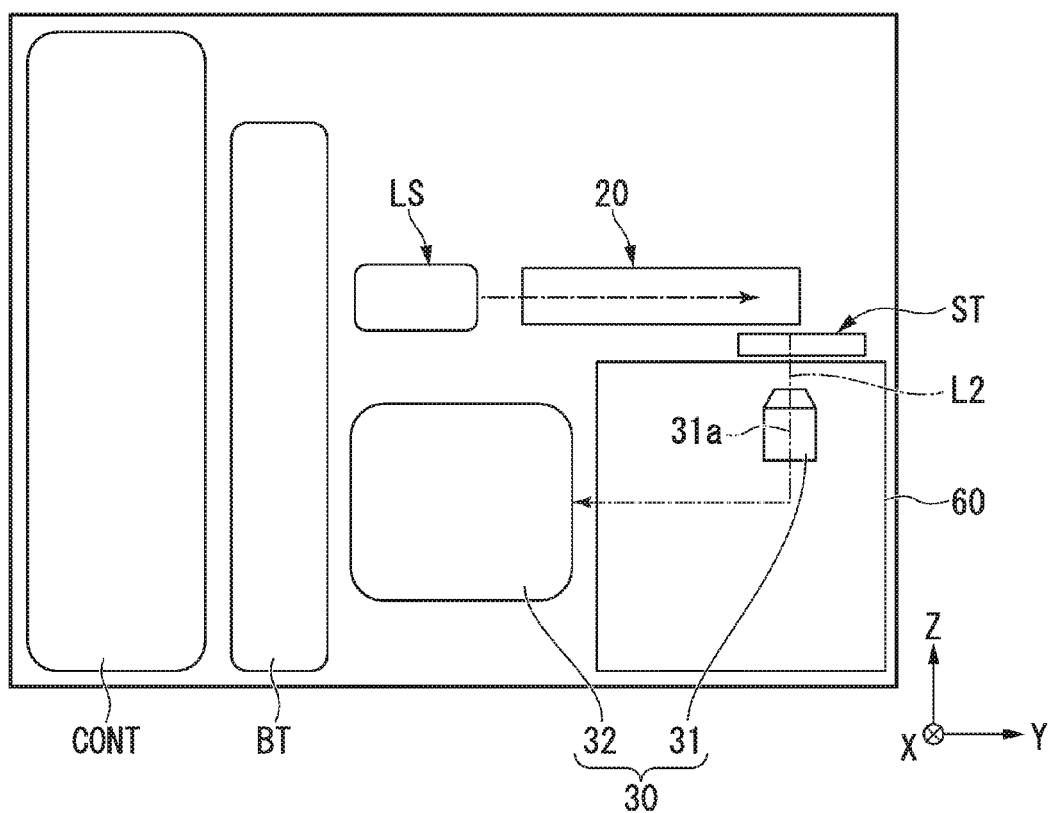
FIG. 2 is a schematic front view of the particle detection device according to an embodiment of the present invention.

FIG. 1 is a schematic plan view of a particle detection device 1 according to an embodiment. FIG. 2 is a schematic front view of the particle detection device 1 according to an embodiment.

The particle detection device 1 takes a fluid device C as the object of detection, shines illumination light L1 onto the fluid device C and observes scattered light L2 from the fluid device C to detect information relating to particles in the fluid device C. The particle detection device 1 includes a light source portion LS, an irradiation portion 20, an adjustment portion CL, a stage portion ST, a detection portion 30 and a control portion CONT. The particle detection device 1 and the fluid device C form a particle detection system 10.

In the following description, a direction orthogonal to an orthogonal plane (not shown) that is orthogonal to a mounting surface STa of the stage portion ST shall be referred to as the x direction (x axis; third direction), the direction parallel to the mounting surface STa and orthogonal to the x direction shall be referred to as the y direction (y axis), and the vertical direction orthogonal to the x direction and the y direction shall be referred to as the z direction (z axis; second direction).

First, the fluid device C, which is the object of detection, shall be described.

The fluid device C in the present embodiment, according to one example, is an electrophoretic analysis chip used in the analysis of a sample. Examples of the sample include cells, extracellular vesicles, microparticles, latex particles (including latex particles that are modified by antibodies as well as those modified by cells), and polymer micelles. In the present embodiment, the case wherein the electrophoretic analysis chip is used as an extracellular vesicle analysis chip for analyzing extracellular vesicles will be described. In the present specification, extracellular vesicles refer to lipid vesicles including exosomes, apoptotic bodies and microvesicles. Herebelow, the extracellular vesicle analysis chip (electrophoretic analysis chip) according to the present embodiment will be described by taking the case of analysis of exosomes as an example.

[Exosomes]

Exosomes are lipid vesicles that have a diameter of approximately 30 to 100 nm, and that are secreted into body fluids such as blood, urine and saliva from various types of cells, such as tumor cells, dendritic cells, T cells and B cells, as fusions of endosomes and the cell membrane.

Abnormal cells such as cancer cells that are present in the body express characteristic proteins on their cell membranes. Exosomes are cell secretions, and express, on their surfaces, proteins from the cells that are the source of secretion.

Therefore, by analyzing proteins expressed on the surfaces of exosomes, it is possible to detect abnormalities in the cells that are the secretion sources. In this case, "the surfaces of exosomes" refer to those portions on the membrane surfaces of lipid vesicles secreted from the cells, where the secreted exosomes come into contact with the environment inside the body.

Since exosomes are detected in the blood that circulates in the body, by analyzing exosomes, abnormalities in the body can be detected without performing a biopsy.

[Analysis of Exosomes]

The analysis of exosomes using an extracellular vesicle analysis chip, according to one example, may be performed as follows. First, the exosomes to be detected are purified. Next, the exosomes are brought into contact with specifically binding substances. In this case, "specifically binding substances" refer to substances that are capable of specifically binding to molecules that are present on the surfaces of exosomes, and these shall be discussed in detail below. Next, an extracellular vesicle analysis chip is used to measure the zeta potentials of the exosomes and to perform the analysis. The present analysis is not limited to exosomes, and may be applied to the analysis of a wide range of extracellular vesicles in general.

(Specifically Binding Substance)

The specifically binding substance may, for example, be an antibody, a modified antibody, an aptamer, a ligand molecule or the like. Examples of antibodies include IgG, IgA, IgD, IgE, IgM and the like. Examples of IgG include IgG1, IgG2, IgG3, IgG4 and the like. Examples of IgA include IgAa1, IgA2 and the like. Examples of IgM include IgM1, IgM2 and the like. Examples of modified antibodies include Fab, F(ab')$_2$, scFv and the like. Examples of aptamers include peptide aptamers, nucleic acid aptamers and the like. Examples of ligand molecules include ligands of receptor proteins or the like when the molecules to be detected that are present on the surfaces of exosomes are receptor proteins. For example, when the molecules present on the surfaces of exosomes are interleukins, G proteins or the like are examples of ligand molecules.

Additionally, the specifically binding substance may be labeled with a labeling substance. Examples of labeling substances include biotin, avidin, streptavidin, neutravidin, glutathione S-transferase, glutathione, fluorescent dyes, polyethylene glycol, and charged molecules such as mellitic acid.

(Purification of Exosomes)

The steps in the present analysis will be described. First, exosomes are purified from a sample containing the exosomes. The sample may, depending on the purpose, be blood, urine, milk, bronchoalveolar lavage fluid, amniotic fluid, malignant exudates, saliva, cell culture solutions or the like. Among these, exosomes can be easily purified from blood and urine.

The method for purification of the exosomes may involve ultracentrifugal separation, ultrafiltration, continuous flow electrophoresis, chromatography, or the use of a μ-TAS (micro-total analysis system) device.

(Reaction Between Exosomes and Specifically Binding Substances)

Next, the exosomes are brought into contact with the specifically binding substances (antibodies, aptamers, etc.). When a molecule that is to be detected is present on the surface of an exosome, a specifically binding substance-exosome complex is formed. By appropriately selecting the specifically binding substance, it is possible to detect abnormalities associated with diseases such as, for example, cancer, obesity, diabetes and neurodegenerative diseases.

(Measurement of Zeta Potential)

As one example, the case wherein an antibody is used as the specifically binding substance will be described. After reacting the exosomes with the antibodies, the zeta potential of the exosomes that have reacted with the antibodies is measured. The zeta potential is the surface charge of a microparticle in a solution. For example, exosomes are negatively charged, whereas antibodies are positively charged. For this reason, the zeta potential of an antibody-exosome complex will be shifted towards the positive compared with the zeta potential of an exosome alone. Therefore, by measuring the zeta potential of exosomes after reacting with antibodies, the expression of antigens on the membrane surfaces of the exosomes can be detected. This is not limited to antibodies, and will similarly apply to positively charged specifically binding substances.

As one example, the zeta potential of exosomes can be calculated by carrying out electrophoresis of the exosomes in a microchannel in an extracellular vesicle analysis chip, optically measuring the electrophoretic speed S of the exosomes, and using the below-given Smoluchowski equation, shown as Equation (1), based on the measured electrophoretic speed S of the exosomes.

$$U=(\varepsilon/\eta)\zeta \quad (1)$$

In Equation (1), U represents the electrophoretic mobility of the exosomes being measured, ε represents the dielectric constant of the sample solution, and η represents the viscosity coefficient of the sample solution. Additionally, the electrophoretic mobility U can be calculated by dividing the electrophoretic speed S by the electric field intensity in the microchannel.

The electrophoretic speed S of exosomes can be measured, in one example, by causing electrophoresis of the exosomes in a microchannel in an extracellular vesicle analysis chip, and in one example, irradiating the exosomes flowing through the microchannel with laser light, and acquiring particle images based on Rayleigh-scattered light. The laser light, as one example, may have a wavelength of 405 nm and have a power of 150 mW.

[Basic Structure of Extracellular Vesicle Analysis Chip]

Figure 3:
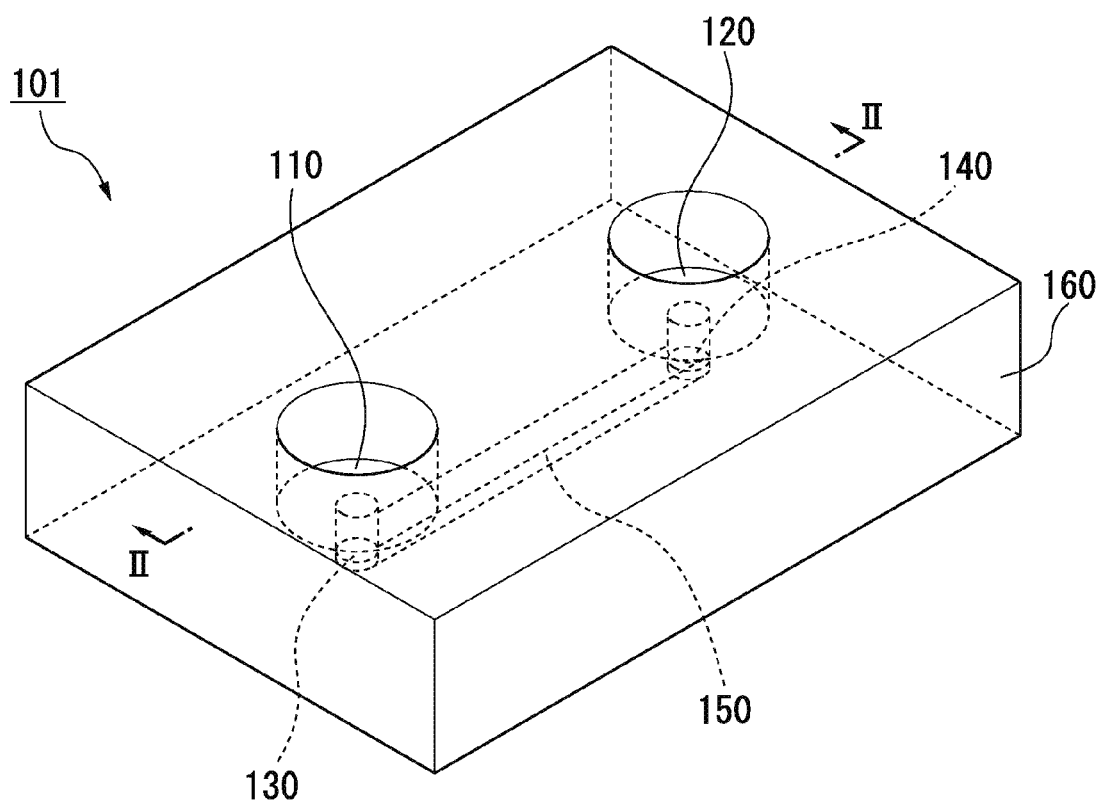
FIG. 3 is a perspective view showing the basic structure of an extracellular vesicle analysis chip according to an embodiment of the present invention.
Figure 4:
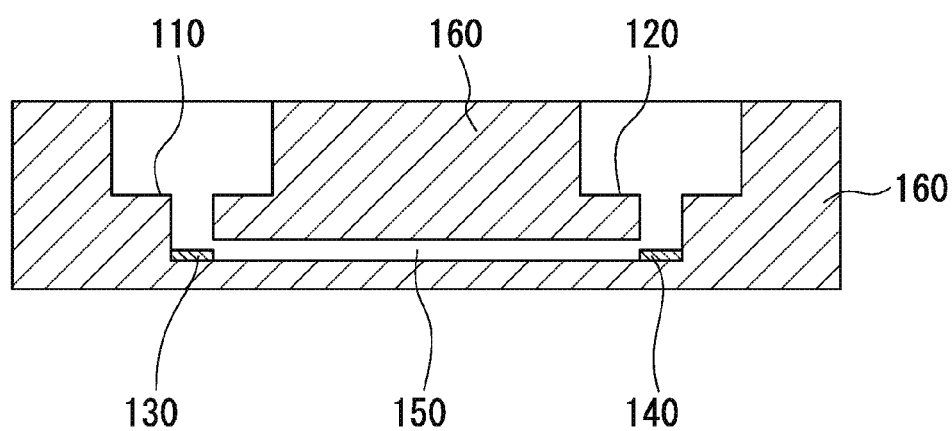
FIG. 4 is a section view along the line II-II in FIG. 3.

FIG. 3 is a perspective view showing the basis structure of an extracellular vesicle analysis chip according to an embodiment. FIG. 4 is a section view along the line II-II in FIG. 3. The extracellular vesicle analysis chip 101 includes a first reservoir 110, a second reservoir 120, a migration channel 150 connecting the first reservoir 110 and the second reservoir 120, and a substrate 160. The migration channel 150 may, for example, be a millichannel or a microchannel. The migration channel 150, in one example, has a width of 200 μm, a height of 400 μm and a length of approximately 10 mm. The migration channel 150 is a channel through which extracellular vesicles, or specifically binding substance-extracellular vesicle complexes (as one example, antibody-exosome complexes), formed by interactions between extracellular vesicles and specifically binding substances that specifically bind to molecules present on the surfaces of the extracellular vesicles, undergo electrophoresis. The specifically binding substance may, in one example, be an antibody, an aptamer, or a substance formed of a combination of an antibody and an aptamer. Examples of aptamers include nucleic acid aptamers and peptide aptamers. Examples of molecules recognized by the specifically binding substances include antigens, membrane proteins, nucleic acids, glycans and glycolipids.

A first end portion of the migration channel 150 is connected to the first reservoir 110. A second end portion of the migration channel 150 is connected to the second reservoir 120. Additionally, the first reservoir 110 and the second reservoir 120 are provided on a substrate 160. The first reservoir 110 has an electrode 130. The second reservoir 120 has an electrode 140. For example, the electrode 130 is provided on a bottom portion of the first reservoir 110, and the electrode 140 is provided on a bottom portion of the second reservoir 120. As shown in FIG. 4, the electrode 130 is provided near an end portion of the migration channel 150, and the electrode 140 is provided near an end portion of the migration channel 150. Additionally, for example, a sample (e.g., exosomes to be analyzed) is introduced to the first reservoir 110, and a buffer solution is introduced to the second reservoir 120. It is also possible to introduce the buffer solution to the first reservoir 110.

The extracellular vesicle analysis chip 101 is capable of measuring the zeta potential of extracellular vesicles. Herebelow, the method of measurement of the zeta potential of exosomes using the present extracellular vesicle analysis chip will be described as an example of a case wherein exosomes are analyzed as the extracellular vesicles or the sample.

First, a sample solution containing the exosomes to be analyzed is introduced to the first reservoir 110.

The exosomes that are to be analyzed may have been reacted with a specifically binding substance. The exosomes, for example, may be extracted from a culture supernatant or blood serum, and the sample solution may, for example, be an exosome suspension wherein exosomes are suspended in a buffer solution such as phosphate-buffered saline (PBS). Next, a sample solution containing exosomes is introduced to the migration channel 150. As one example, exosomes may be introduced to the migration channel 150 by connecting a syringe with the second reservoir 120 and drawing up the sample solution. Next, the buffer solution is entered into the first reservoir 110 and the second reservoir 120. The liquid levels (liquid surface heights) of the first reservoir 110 and the second reservoir 120 are adjusted and aligned by a liquid level adjusting means to be described below, and thereby, it is possible to prevent the generation of a hydrostatic pressure flow in the migration channel 150 and improve the accuracy of the zeta potential measurement. Subsequently, a voltage is applied between the electrodes 130 and 140 by means of a control portion (e.g., the control portion CONT to be described below, a computer, or the like), so as to induce electrophoresis of the exosomes. As one example, the control portion applies a voltage providing an electric field intensity of approximately 50V/cm for approximately 10 seconds.

During the electrophoresis, the migration channel 150 is irradiated with laser light, and scattered light that has passed through the exosomes, which is the light exiting from the migration channel 150, is collected using an objective lens or the like, and the exosomes or the specifically binding substance-exosome complexes are imaged using a light-receiving sensor (e.g., a high-sensitivity camera). The magnification of the objective lens, in one example, is approximately 60 times. In one example, the wavelength of the laser is 405 nm, and the power of the laser is 150 mW.

Subsequently, the control portion calculates the electrophoretic speed S of the exosomes or the specifically binding substance-exosome complexes on the basis of the captured image. Then, the control portion divides the electrophoretic speed S by the electric field intensity to calculate the electrophoretic mobility U. Subsequently, the control portion uses the above-given Smoluchowski equation to calculate the zeta potential of the exosomes or the specifically binding substance-exosome complexes.

By using the extracellular vesicle analysis chip according to the present embodiment, it is possible to measure not only the average value of the zeta potential for the specifically binding substance-exosome complexes, but the zeta potentials of the specifically binding substance-exosome complexes on a single particle level. For this reason, even in cases where the average value of the zeta potential would suggest that exosomes having molecules (for example, antigens or the like) that are recognized by a specifically binding substance are not present, it is still possible to detect exosomes having such antigens if they are present as a minor population.

[Structure of Fluid Device C]

Figure 5:
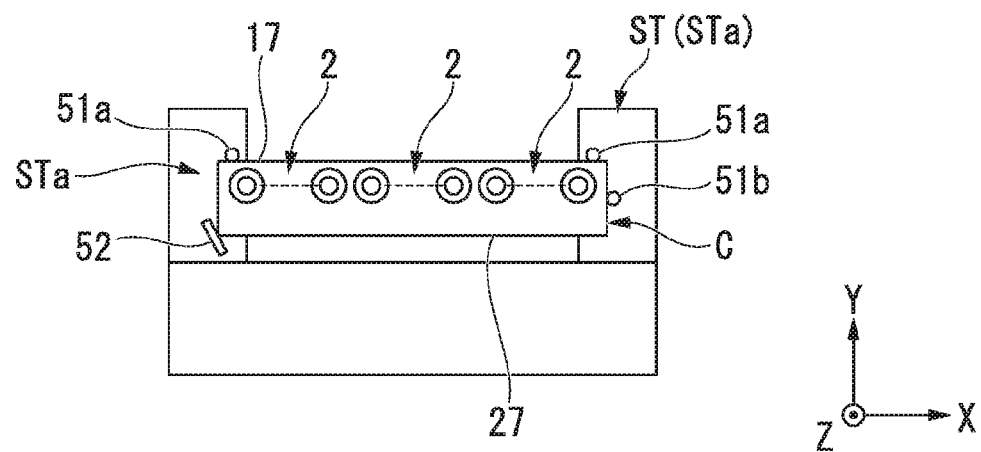
FIG. 5 is a plan view of a fluid device according to an embodiment of the present invention.
Figure 6:
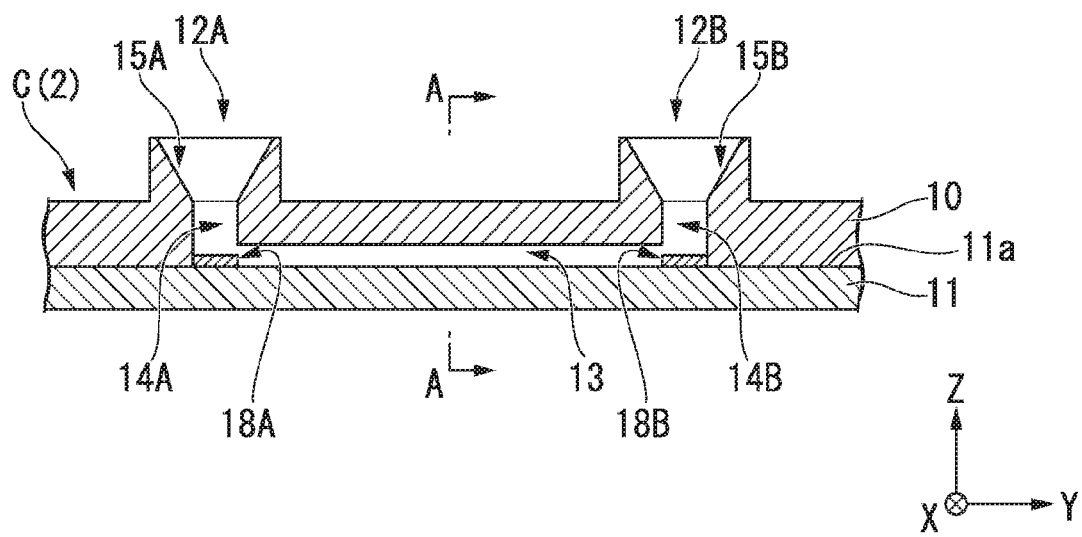
FIG. 6 is a partial section view of a chip that has been partially cut away at the YZ plane.
Figure 7:
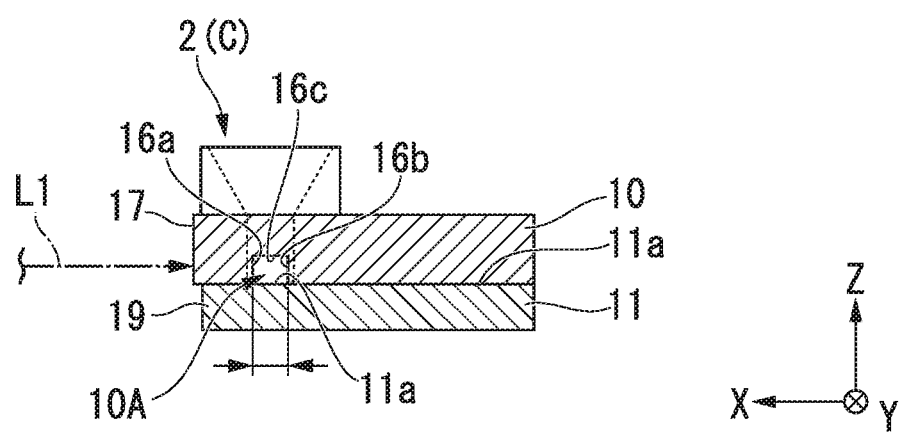
FIG. 7 is a section view along the line A-A in FIG. 6.

FIG. 5 is a plan view wherein a fluid device C is mounted on mounting surfaces STa of a stage portion ST according to an embodiment. FIG. 6 is a partial section view of the fluid device C according to the embodiment, partially cut along the yz plane. FIG. 7 is a section view along the line A-A in FIG. 6.

As shown in FIG. 5, the fluid device C is formed so as to be rectangular in plan view. As shown in FIG. 6, the fluid device C comprises a reservoir member (first substrate) 10 and a bottom plate (second substrate) 11 that are sequentially stacked in the z direction. For example, the fluid device C in the present embodiment has a laminated structure (laminate) formed at least by a reservoir member 10 and a bottom plate 11.

In this case, the lamination structure of the fluid device C is a two-layered structure. Additionally, for example, the laminated structure of the fluid device C is formed by bonding together a reservoir member 10 and a bottom plate 11.

The reservoir member 10 is formed of a material that is capable of elastically deforming in at least one direction due to an external force or the like. The material of the reservoir member 10, in one example, is an elastomer, such as silicone rubber or PDMS (polydimethylsiloxane). The bottom plate 12 is formed from a material that transmits scattered light L2 generated by irradiation with illumination light L1. The bottom plate 12, in one example, is formed from a glass material.

The fluid device C includes a plurality (three in FIG. 5) of lanes 2 arranged in the lengthwise direction (y direction). Each lane 2 includes a first reservoir 12A, a second reservoir 12B, a channel 13 and electrodes 18A and 18B. The first reservoir 12A and the second reservoir 12B are arranged so as to be spaced apart in the y direction. For example, the first reservoir 12A and the second reservoir 12B are arranged so as to be spaced apart in the flow direction of the channel 13. The plurality of lanes 2 may also be arranged in the height direction (z direction). In this case, the solution may be injected from the lengthwise direction (x direction), or injected from the y direction. There may, for example, be a plurality of irradiation light sources, and each light source may irradiate the microparticles flowing through a lane 2 at a corresponding height. Additionally, the microparticles flowing through the lanes 2 may also be irradiated by changing the direction of illumination from at least one irradiation light source.

The first reservoir 12A includes a holding space 14A having a circular cross-section in a plane parallel to the xy plane and extending in the z direction, and a feeding portion 15A in the shape of a funnel having a diameter that becomes gradually larger in the +z direction from the +z-side of the holding space 14A. The end of the holding space 14A on the −z-side opens onto the bottom plate 11. The holding space 14A is connected to the channel 13.

The second reservoir 12B includes a holding space 14B having a circular cross-section in a plane parallel to the xy plane and extending in the z direction, and a feeding portion 15B in the shape of a funnel having a diameter that becomes gradually larger in the +z direction from the +z-side of the holding space 14B. The end of the holding space 14B on the −z-side opens onto the bottom plate 11. The holding space 14B is connected to the channel 13.

The channel 13 is an electrophoresis channel (a channel for electrophoresis). The channel 13 extends in they direction, which is the lengthwise direction of the fluid device C. The channel 13 is provided so as to connect the holding space 14A and the holding space 14B on the surface on the side facing the bottom plate 11. The channel 13, as shown in FIG. 7, is enclosed by a groove portion 10A formed in the reservoir member 10, and a surface (second surface) 11a of the bottom plate 11. As a result, the channel 13 is formed so as to have a rectangular cross-section. The groove portion 10A is formed so as to be enclosed by side surfaces (first surface) 16a, 16b that face each other in the x direction and a bottom surface (second surface) 16c that faces the surface 11a of the bottom plate 11 in the z direction. The side surfaces 16a, 16b, the bottom surface 16c and the surface 11a forming the groove portion 10A are mirror-finished. The first surfaces include a side surface 16a which is a first side surface and a side surface 16b which is a second side surface. The side surface 16a and the side surface 16b face each other and are separated from each other in the x direction, which is the first direction.

In the optical axis direction (incidence direction) of the illumination light L1, which is the width direction of the fluid device C, the lanes 2 are arranged so as to deviate from the center towards the side closer to the +x-side end surface 17. In the width direction (the x direction in FIG. 5) of the fluid device C, which is the optical axis direction of the incident illumination light L1, the lanes 2 are arranged so as to deviate from the center towards the side closer to the incidence-side end surface 17 of the illumination light L1. The end surface 17 is mirror-finished in they direction in at least the range over which the lanes 2 are provided. The channel 13, in one example, is formed so as to have approximate dimensions of a width of 200 μm, a height (depth of the groove portion 10A) of 400 μm and a length of 10 mm.

An electrode 18A facing the holding space 14A is provided on the surface 11a of the bottom plate 11. An electrode 18B facing the holding space 14B is provided on the surface 11a of the bottom plate 11. Examples of the materials of the electrode 18A and the electrode 18B include gold, platinum and carbon. As shown in FIG. 7, the end surface (second end surface) 19 positioned on the incidence-side of the illumination light L1 in the bottom plate 11 is separated from the position of the end surface 17 of the reservoir member 10, in the x direction, to the −x-side, which is the side opposite to the side on which the illumination light L1 is incident.

Returning to FIG. 1, as the illumination light L1, the light source portion LS, in one example, emits laser light that is oriented in the z direction, having a beam diameter (the diameter at which the intensity becomes $1/e^2$ of the peak value) of 0.8 mm at a power of 150 mW, and a wavelength of 405 nm, as a wavelength that does not adversely affect the particles, as mentioned above. The illumination light L1 may be polarized (e.g., linearly polarized) or unpolarized, but in the present embodiment, vertically polarized light is used, and a configuration having no directionality of Rayleigh scattering is employed.

The illumination light L1 is used to irradiate the fluid device C along an optical axis extending in the above-mentioned direction intersecting an orthogonal plane. In the present embodiment, the optical axis of the illumination light L1 is parallel to the x direction. The illumination light L1 of the present embodiment is used to irradiate the fluid device C on an optical axis extending in the x direction.

Figure 8:
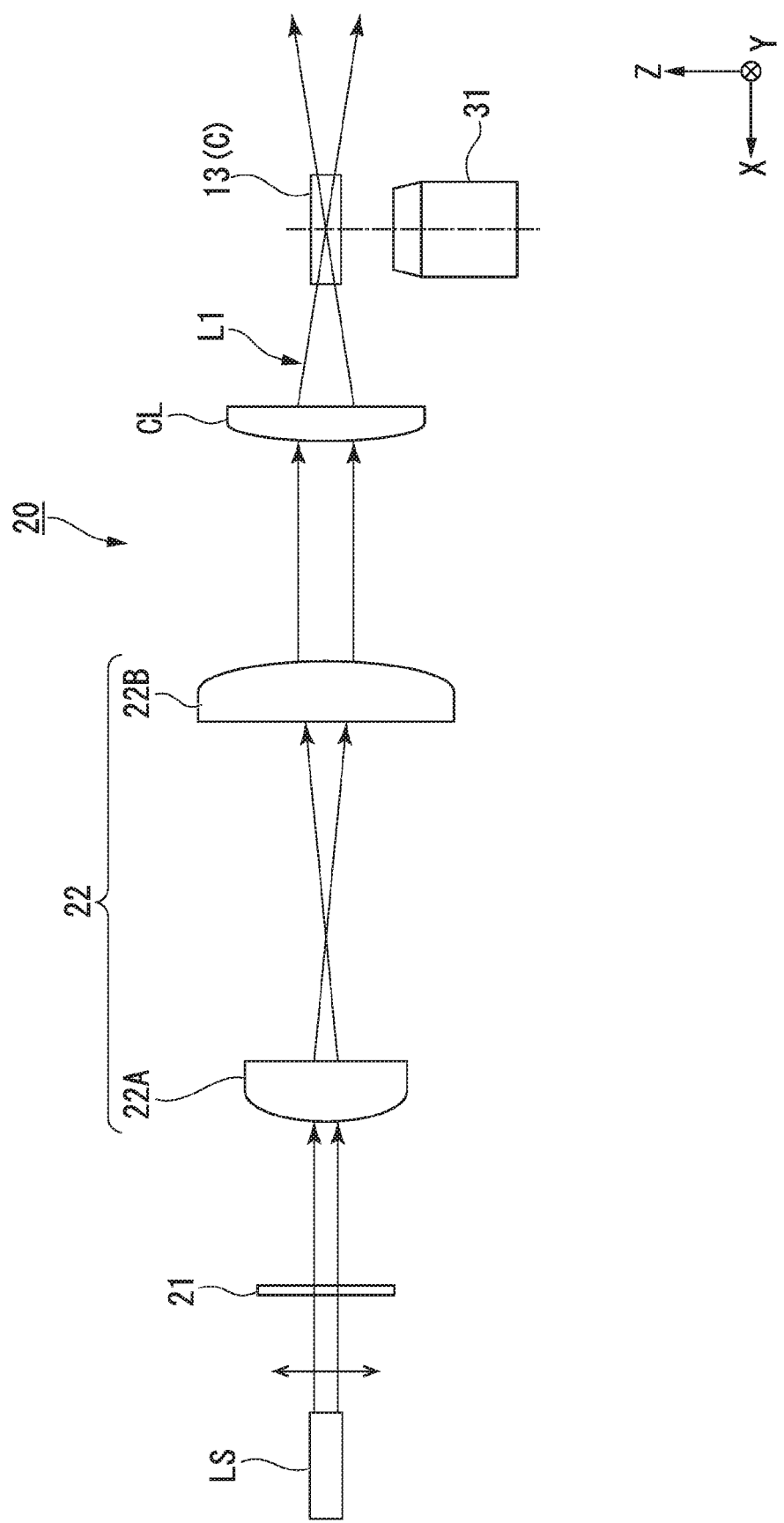
FIG. 8 is a diagram showing the schematic structure of an irradiation portion and an adjustment portion.

FIG. 8 is a diagram showing the schematic structure of the irradiation portion 20 and the adjustment portion CL according to an embodiment. The irradiation portion 20 includes a λ/2-plate 21 and an expander lens 22 sequentially arranged along the optical axis of the illumination light L1. While the light source portion LS and the irradiation portion 20 shown in FIG. 1 are oriented so that the optical axis of the illumination light L1 extends in the y direction, the illumination light L1 that finally irradiates the fluid device C (channel 13) has an optical axis that is aligned with the x direction. For this reason, the illumination light L1 shown in FIG. 8 is illustrated as having an optical axis aligned with the x direction.

The direction of polarization of the illumination light L1 emitted by the light source portion LS is rotated to be aligned with the y direction by passing through the λ/2-plate 21. If the light source portion LS emits illumination light L1 that is polarized in the y direction, the λ/2-plate 21 is unnecessary. The expander lens 22 includes cylindrical lenses 22A and 22B that face each other. The cylindrical lenses 22A and 22B do not have any power in they direction, so the width of the illumination light L1 in the y direction remains constant. The width of the illumination light L1 in the z direction becomes greater or smaller in accordance with the distance in the optical axis direction of the cylindrical lenses 22A and 22B. In the present embodiment, the expander lens 22 expands the width of the illumination light L1 in the z direction to be, in one example, twice as large.

The adjustment portion CL adjusts the incident illumination light L1 having the width in the z direction enlarged by the expander lens 22. The adjustment portion CL is arranged on the optical path between the light source portion LS and an objective lens 31. Additionally, the adjustment portion CL is arranged on the optical path between the λ/2-plate 21 or the expander lens 22 and the objective lens 31. The adjustment portion CL may include a drive mechanism, and the light convergence point may be able to be adjusted by moving the adjustment portion CL. The adjustment portion CL may, for example, be able to be driven in the x direction.

Figure 9:
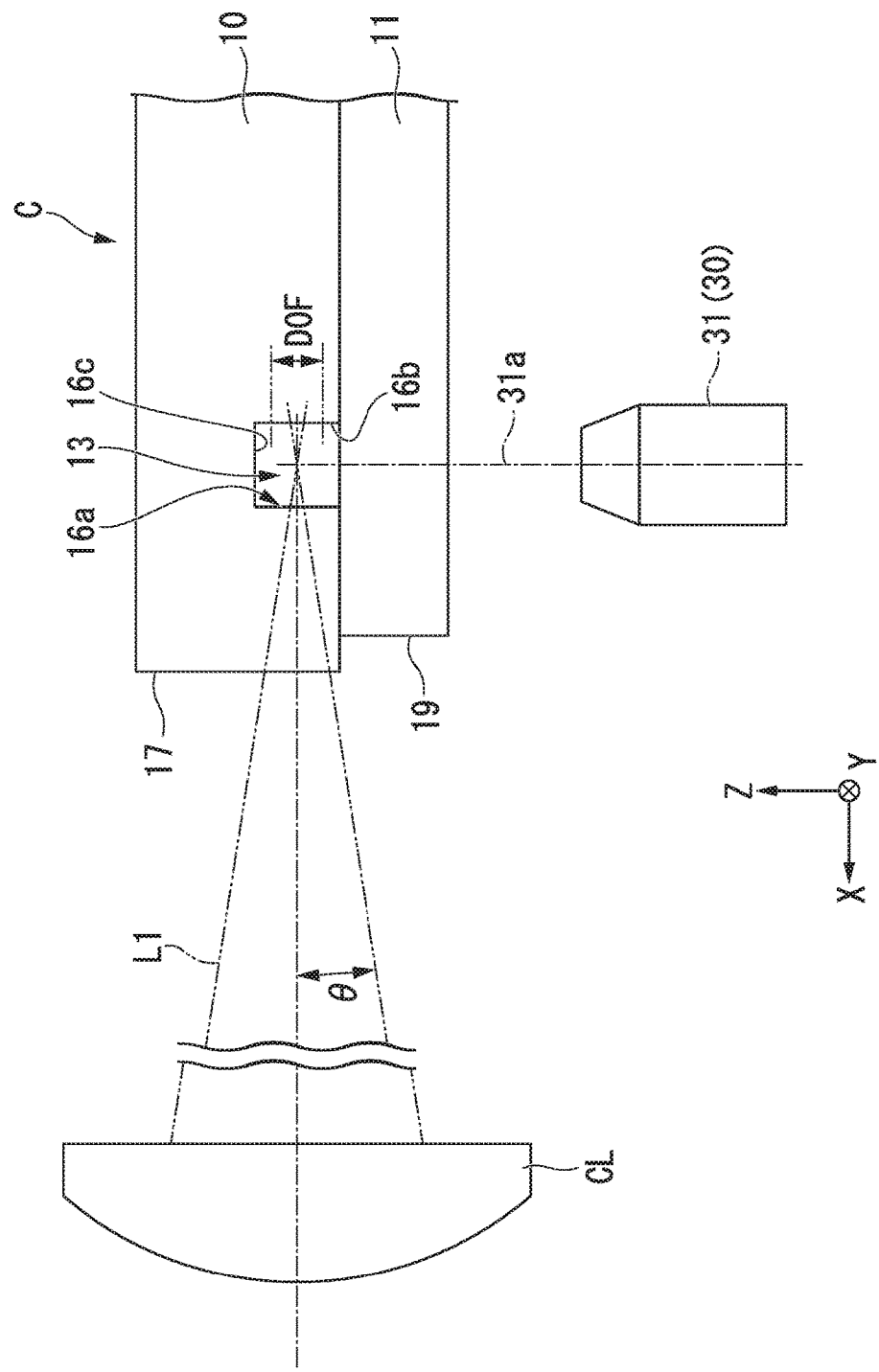
FIG. 9 is a partial detailed view of an adjustment portion and a fluid device according to an embodiment of the present invention.

In this case, even when using chips in which the positions of the channels 13 are different, it is possible to make adjustments so that the light convergence point is positioned within the channel 13. Additionally, adjustments can be made to substantially align the light convergence point with the center of the channel 13, or to substantially align the light convergence point with the central portion of the detection portion. FIG. 9 is a partial detailed view of an adjustment portion CL and a fluid device C according to an embodiment.

The adjustment portion CL, in one example, is formed of a cylindrical lens. The adjustment portion CL adjusts the convergence angle of the illumination light L1 so that the width of the illumination light L1 in the z direction is minimized inside the channel 13, and so that the region of passage of the illumination light L1 at a position on the illumination light incidence-side side surface 16a of the channel 13 converges so as to be limited to be within the side surface 16a. The adjustment portion CL adjusts the convergence angle of the illumination light L1 so that the width of the illumination light L1 in the z direction is minimized inside the channel 13, and so that the irradiation region of the illumination light L1 at a position on the illumination light incidence-side side surface 16a of the channel 13 is focused to be within the side surface 16a. Additionally, the adjustment portion CL adjusts the convergence angle of the illumination light L1 so that the region of passage of the illumination light L1 (irradiation light flux) at a position on the illumination light exit-side side surface 16b of the channel 13 converges so as to be limited to be within the side surface 16b. The adjustment portion CL adjusts the convergence angle of the illumination light L1 so that the irradiation region of the illumination light L1 (irradiation light flux) at a position on the illumination light exit-side side surface 16b of the channel 13 is focused to be within the side surface 16b. Additionally, the adjustment portion adjusts the convergence angle of the illumination light L1 so that the irradiation region of the illumination light L1 at a position on the end surface 17 of the reservoir member 10 converges to be within the end surface 17. Furthermore, the adjustment portion CL adjusts the convergence angle of the illumination light L1 so that the convergence point is present in a detection region inside the channel 13.

For example, the convergence angle is such that the illumination light flux of the illumination light L1 outside the depth of focus at the detection portion 30 in the detection region of the channel 13 is smaller than the illumination light flux inside the depth of focus. The above-mentioned orthogonal surface, for example, includes the end surface 17 of the reservoir member 10, the side surface 16a of the illumination light incidence-side side surface 16a of the channel 13, or the illumination light exit-side side surface 16b of the channel 13.

For illumination light L1 in the optical axis direction (x direction), when the width in the z direction is a minimum width $\omega_0$ at the center (x=0) of the channel 13, and $\theta$ represents the convergence angle of the illumination light L1 in the medium inside the channel 13, λ represents the wavelength of the illumination light L1, $\omega(x, \theta)$ represents the beam width in the z direction at the position x and with a convergence angle $\theta$, $M^2$ represents the beam profile factor of the illumination light L1 and xL represents the distance from the x-direction position where the minimum width $\omega_0$ occurs to the side surface 16a, in the following equation (1) and equation (2), equation (3) must be satisfied.

$$\omega(x, \theta) = \omega_0 \cdot \sqrt{1 + \left(\frac{\lambda x M^2}{\pi \omega_0^2}\right)^2} \quad (1)$$

$$\omega_0 = \frac{\lambda M^2}{\pi \theta} \quad (2)$$

$$\frac{d\omega(x_L, \theta)}{d\theta} = 0 \quad (3)$$

Therefore, as the adjustment portion CL, an adjustment portion CL that at least satisfies Equations (1) to (3), and that has optical properties that are adjusted so as to make the illumination light L1 converge at a convergence angle $\theta$ such that the beam width $\omega(xL, \theta)$, when x=xL, is smaller than the length of the side surface 16a in the z direction, so that the illumination light L1 converges to be within the side surface 16a, is installed.

When the illumination light L1 is a Gaussian beam, the beam width $\omega(x, \theta)$ in the above-mentioned Equations (1) to (3) is defined as the width at which the intensity of the illumination light L1 becomes $1/e^2$ with respect to the peak value. Even when the convergence angle $\theta$ satisfies the Equations (1) to (3), since illumination light L1 having an intensity of $1/e^2$ or less with respect to the peak value will be incident at a position on the side surface 16a outside the beam width $\omega(xL, \theta)$, the beam width of the illumination light L1 having an intensity of $1/e^2$ or less with respect to the peak value is also considered when setting the convergence angle $\theta$.

Figure 10:
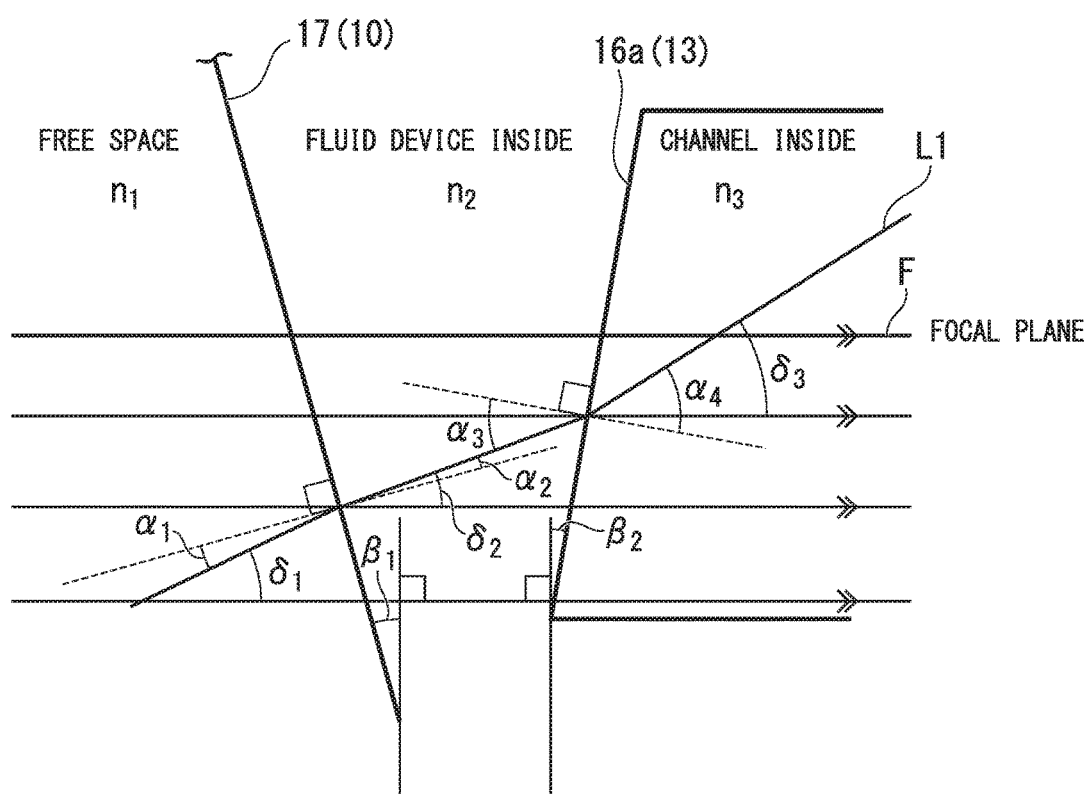
FIG. 10 is a diagram schematically showing an optical path of illumination light according to an embodiment of the present invention.

Additionally, in order to make the entire channel 13 the detection region in the optical axis direction (x direction) of the illumination light L1 by means of the detection portion 30, the depth of focus DOF of the detection portion 30 must be within the light flux of the illumination light L1 across the entire channel 13. In order for the depth of focus DOF of the detection portion 30 to be within the light flux of the illumination light L1, it is necessary to take into consideration the inclination of the end surface 17 of the reservoir member 10 and the side surface 16a of the channel 13 with respect to the optical axis. FIG. 10 is a diagram schematically showing the optical path of the illumination light L1 passing through the end surface 17 of the reservoir member 10 and the side surface 16a of the channel 13 according to an embodiment. In order for the depth of focus DOF (see FIG. 9) of the detection portion 30 to be within the light flux of the illumination light L1 across the entire width of the channel 13, the following Equation (4) must be satisfied.

$$|\delta_3| \leq \left|\frac{\omega(x_L, \theta) - DOF/2}{x_L}\right| \quad (4)$$

Here, the angle δ3 is the elevation angle of the illumination light axis as seen from the focal plane F, and the counterclockwise direction from the focal plane F is the positive direction. On the other hand, the following relationships are established between the angle of incidence and the angle of exit at the interfaces, the angles of inclination of the end surface 17 of the reservoir member 10 and the side surface 16a of the channel 13 with respect to the yz plane, the elevation angles of the illumination light flux with respect to the focal plane F in air, in the material of the fluid device C and in the channel, and the refractive indices of the medium on the outside of the fluid device C, the material of the fluid device C and the medium inside the channel 13.

$n1 \sin \alpha1 = n2 \sin \alpha2$ $n2 \sin \alpha3 = n3 \sin \alpha4$ $\alpha1 + \beta1 = \delta1$ $\alpha2 + \beta1 = \delta2$ $\alpha3 + \beta2 = \delta2$ $\alpha4 + \beta2 = \delta3$ Here,
$\alpha1$: the angle of incidence of the illumination light L1 from free space into the end surface 17 of the reservoir member 10;
$\alpha2$: the angle of exit of the illumination light L1 from the end surface 17 into the reservoir member 10;
$\alpha3$: the angle of incidence of the illumination light L1 from inside the reservoir member 10 to the side surface (wall surface) 16a of the channel 13;
$\alpha4$: the angle of exit of the illumination light L1 from the side surface 16a to the inside of the channel 13;
$\beta1$: the angle of inclination of the end surface 17;
$\beta2$: the angle of inclination of the side surface 16a;
$\delta1$: the elevation angle of the illumination light L1 from the focal plane F in free space;
$\delta2$: the elevation angle of the illumination light L1 from the focal plane F in the reservoir member 10;
$\delta3$: the elevation angle of the illumination light L1 from the focal plane F in the channel 13;
n1: the refractive index of the free space medium;
n2: the refractive index of the material of the reservoir member 10; and
n3: the refractive index of the medium inside the channel 13.
Angle of incidence and angle of exit: the angle with respect to the normal to the end surface 17 and the side surface 16a;
Angle of inclination: the angle with respect to the normal to the focal plane F; and
Elevation angle: the angle from the focal plane F.
Additionally, the signs are such that the counterclockwise direction is positive.

Based on the above-given equations, the elevation angle $\delta3$ of the illumination light L1 in the channel 13 can be represented by the following Equation (5).

$$\delta_3 = \sin^{-1}\left(\frac{n_2}{n_3}\sin\left(\left(\sin^{-1}\left(\frac{n_1}{n_2}\sin(\delta_1 - \beta_1)\right)\right) + \beta_1 - \beta_2\right)\right) + \beta_2 \quad (5)$$

Therefore, in order for the depth of focus DOF of the detection portion 30 to be within the light flux of the illumination light L1 across the entire width of the channel 13 in the x direction, the following Equation (6) must be satisfied.

$$\left|\sin^{-1}\left(\frac{n_2}{n_3}\sin\left(\left(\sin^{-1}\left(\frac{n_1}{n_2}\sin(\delta_1 - \beta_1)\right)\right) + \beta_1 - \beta_2\right)\right) + \beta_2\right| \leq \quad (6)$$

$$\left|\frac{\omega(x_L, \theta) - DOF/2}{x_L}\right|$$

Therefore, the angle of inclination of the end surface 17 of the reservoir member 10 and the side surface 16a of the channel 13, and the elevation angle $\delta3$ of the illumination light L1, must be selected, produced and adjusted so as to satisfy Equation (6) in accordance with the refractive index n1 of the free space medium, the refractive index n2 of the material of the reservoir member 10, and the refractive index n3 of the medium inside the channel 13.

The stage portion ST is moved in the x direction, the y direction and the z direction by driving a stage driving portion 60 as shown in FIG. 2. The driving of the stage driving portion 60 is controlled by the control portion CONT. As shown in FIG. 5, the stage portion ST includes mounting surfaces STa on which the fluid device C is to be mounted. The mounting surfaces STa are surfaces that are parallel to the xy plane. The mounting surfaces STa are arranged so as to be spaced apart in the y direction. The mounting surfaces STa support, from the −z-side, both y direction end portions of the fluid device C, where the lanes 2 are not provided. The fluid device C is supported on the mounting surfaces STa so that the areas where the lanes 2 are provided do not obstruct the observation from the −z side by the detection portion 30. Additionally, since the stage portion ST is not present on the optical path of the illumination light L1 until the lanes 2 in the fluid device C are irradiated, it is possible to suppress part of the illumination light L1 that is incident on the fluid device C from entering into the stage portion ST and adversely affecting the particle detection to be described below.

Protruding fixation pins 51 are provided on the mounting surfaces STa. The fixation pins 51 are formed from two fixation pins 51a that are in abutment with a long side of the fluid device C, and one fixation pin 51b that is in abutment with the short side of the fluid device C. The fixation pins 51a are respectively disposed near either side of the fluid device C in the y direction. The fixation pin 51b is in abutment with the short side positioned on the +y side. A pressing piece 52 is provided at a corner portion positioned diagonally from the corner portion disposed between the fixation pin 51b and the fixation pin 51a that is positioned on the +y side. The pressing piece 52 presses the fluid device C against the stage portion ST in the diagonal direction. The pressed fluid device C, by being in abutment with the fixation pins 51a and 51b, is fixed so as to be positioned on the stage portion ST with respect to the x and y directions such that the channel 13 (lanes 2) is arranged parallel to the y direction.

The detection portion 30 includes an objective lens 31 and an imaging portion 32. The objective lens 31 is disposed on the −z side of the stage portion ST and the fluid device C. As shown in FIG. 9, the objective lens 31 is disposed at a position where the detection axis 31a passes through the center of the channel 13 in the x direction. The detection axis 31a is orthogonal to the optical axis of the illumination light L1. The imaging portion 32, in one example, includes an EMCCD (electron multiplying charge coupled device) camera, and captures images of the incident light. The imaging portion 32 obtains image information of sideways-scattered light that is incident via the objective lens 31.

The control portion CONT generally controls the particle detection device 1 and the particle detection system 100. The control portion CONT controls the movement of the stage portion ST and the fluid device C by means of the stage driving portion 60. The control portion CONT controls a power supply portion (application portion) BT so as to cause electrodes 18A and 18B to apply an electric field in a direction along the channel 13. The control portion CONT, as a determination portion of the detection portion 30, determines information relating to particles inside the channel 13 on the basis of image information captured by the imaging portion 32.

The method for detecting particles using the particle detection device 1 and the particle detection system 100 having the above-described configuration will be described.

The particle detection method of the present embodiment includes a mounting step, an introduction step, an irradiation step and a detection step.

The mounting step is a step of mounting the fluid device C on a mounting surface STa of a stage portion ST.

Specifically, as shown in FIG. 5, by pressing the fluid device C in the diagonal direction by means of the pressing piece 52, the fluid device C is pressed against the fixation pins 51a and 51b, and is mounted on the mounting surfaces STa so as to be positioned on the stage portion ST such that the channel 13 (lanes 2) is arranged parallel to the y direction.

The introduction step is a step of introducing a sample containing particles into the holding spaces 14A and 14B and the channel 13 of the fluid device C. The sample, in one example, may be an exosome suspension wherein exosomes are suspended in a buffer solution (medium) such as a phosphate buffer.

After the sample is introduced into the channel 13, the control portion CONT drives the stage driving portion 60 and positions a lane 2 that is to be detected on the optical path of the illumination light L1 and on the detection axis 31a of the detection portion 30. When the lane 2 to be detected is moved to the detection position, the control portion CONT controls the power supply portion BT so as to apply an electric field between the electrode 18A and the electrode 18B and thereby imparts a force to cause electrophoresis of the exosomes along the channel 13. In one example, the control portion CONT applies a voltage having an electric field intensity of approximately 50 V/cm for approximately 10 seconds. The direction of migration of the exosomes is parallel to the y direction.

The irradiation step is a step of irradiating the channel 13 of the fluid device C with the illumination light L1 in a direction parallel to the x direction.

The irradiation portion 20 for emitting the illumination light L1 and the adjustment portion CL cause emission of the illumination light L1 in the form of a sheet beam having a width that is constant in the y direction but that converges in the z direction by a convergence angle θ satisfying the above-mentioned Equation (1) to Equation (6). The minimum beam thickness (the beam width in the z direction) of the illumination light L1, in one example, is 10 μm. The direction of the minimum beam thickness (the beam width in the z direction) of the illumination light L1 is in the z direction in FIG. 7 and FIG. 9, or in a direction parallel to the z direction. The direction of the minimum beam thickness (the beam width in the z direction) of the illumination light L1 is a direction that is different from the channel direction and the optical axis direction of the illumination light L1 at the incident surface (end surface 17 and side surface 16a), and is a direction orthogonal to the optical axis direction and the channel direction. The channel direction is the direction of extension of the channel 13. The channel direction is the direction of flow of the fluid in the channel 13.

The emitted illumination light L1 passes sequentially through a first end surface (illumination light incidence-side end surface) 17 of the fluid device C, a side surface (illumination light incidence-side side surface) 16a of the channel 13, the inside of the channel 13, the side surface (illumination light exit-side side surface) 16b of the channel 13, and the second end surface (illumination light exit-side end surface) 27 of the fluid device C (see FIG. 5). The illumination light L1 is emitted in a direction that is orthogonal to the direction of movement of the exosomes.

The emitted illumination light L1, as shown in FIG. 9, converges so that the width in the z direction becomes the smallest within the channel 13, and converges so that the region of passage of the illumination light flux at the position of the side surface 16a of the channel 13 is limited to be within the side surface 16a. Furthermore, the emitted illumination light L1 converges so that the region of passage of the illumination light flux at a position on the illumination light exit-side side surface 16b of the channel 13 is limited to be within the side surface 16b. The convergence angle of the illumination light L1 is adjusted so that the irradiation region at a position on the side surface 16a is focused to be within the side surface 16a, and the irradiation region at a position on the side surface 16b is focused to be within the side surface 16b. Additionally, the emitted illumination light L1 has a convergence point within the detection region of the detection portion 30 in the channel 13.

The detection step involves observing (imaging) and detecting scattered light generated from particles inside the channel 13 upon irradiation by the illumination light L1 in a direction parallel to the x direction. Since the detection axis 31a of the objective lens 31 in the detection portion 30 is orthogonal to the optical axis of the illumination light L1, the detection portion 30 detects sideways-scattered light generated from the particles. The detection portion 30 detects light scattered in the z direction, perpendicular to the x direction, by irradiation with the illumination light L1 emitted in a direction parallel to the x direction. An image of the particles for which the scattered light was observed is captured by the imaging portion 32. The control portion CONT determines information (e.g., the particle size and the movement speed of the particles) relating to the particles on the basis of the image information captured by the imaging portion 32.

For example, the electrophoretic speed of the exosomes can be determined from two images captured with a time difference. The control portion CONT calculates the electrophoretic mobility by using the determined electrophoretic speed and the electric field intensity applied between the electrodes 18A and 18B (the electric field intensity inside the channel 13). Furthermore, the control portion CONT can determine the zeta potential of the exosomes using the calculated electrophoretic mobility and the dielectric constant and the viscosity coefficient of the medium inside the channel 13.

In the present embodiment, sideways-scattered light generated from the particles is detected, so image information having little noise can be obtained compared to cases in which forward-scattered light is received. Additionally, for example, if the illumination light L1 is not adjusted so that the region of passage of the illumination light flux at the position of the side surface 16a is limited to be within the side surface 16a, and a portion K of the illumination light L1 enters the interior of the channel 13 through the bottom plate 11, there is a possibility of scattered light being generated at the side surface 16*b* or the bottom surface 16*c*. The signal intensity of the scattered light generated at the side surface 16*b* or the bottom surface 16*c* is several orders of magnitude greater than the signal intensity of the scattered light generated by the particles being observed, and exceeds the dynamic range of the imaging portion 32. When observing the particles, there is a possibility that the scattered light generated by the side surface 16*b* or the bottom surface 16*c* (hereinafter referred to as the wall surfaces) will saturate the imaging portion 32. Additionally, when this scattered light is generated over a wide range in the z direction, it will spread due to defocusing, and the scattered light will greatly erode the observation range inside the channel 13 at the imaging portion 32. In the present embodiment, the illumination light L1 is converged so that the region of passage of the illumination light L1 at the position of the side surface 16*a* is limited to be within the side surface 16*a*, and the region of passage of the illumination light L1 at the position of the end surface 17 is limited to be within the end surface 17, so the generation of scattered light of high signal intensity can be suppressed. For this reason, in the present embodiment, information relating to the particles inside the channel 13 can be detected with a high level of accuracy.

Additionally, the scattered light from the particles outside the depth of focus DOF of the detection portion 30 can be defocused to become background light, so that the shapes of the particles cannot be detected. In the present embodiment, the width in the z direction is the smallest inside the channel 13, and the background light outside the observation region inside the channel 13 is suppressed, making it possible to detect particles illuminated with the illumination light L1 with a high level of accuracy. Additionally, in the present embodiment, the end surface 17 is mirror-finished, so it is possible to suppress situations in which the light scattered by the end surface 17 becomes noise and has an adverse influence on the particle detection accuracy. Additionally, in the present embodiment, the optical axis can be easily adjusted because the illumination light L1 is incident at an angle orthogonal to the end surface 17. Furthermore, in the present embodiment, the end surface 19 of the bottom plate 11 is separated from the end surface 17 of the reservoir member 10 towards the side opposite from the illumination light L1 incidence side, so it is possible to avoid cases in which part of the illumination light L1 is incident on the end surface 19 before being incident on the end surface 17.

Preferred embodiments of the present invention have been described above with reference to the attached drawings, but the present invention is not to be construed as being limited to said embodiments. The shapes and combinations of the constituent elements indicated in the above-described examples are merely exemplary, and various modifications are possible, in accordance with design requirements or the like, within a range not departing from the gist of the present invention.

For example, in the above-described embodiment, the particles are caused to move inside the channel 13 by imparting a force by means of an electric field, but there is no such limitation, and it is possible to use configurations wherein the particles are moved in a predetermined direction by imparting a flow to the medium, or configurations wherein a force is not imparted to move the particles in a predetermined direction.

Additionally, in the above-described embodiments, scattered light generated from the particles in the −z direction is detected, but there is no such limitation, and for example, it is possible to detect light scattered to the +y side, to the −y side or to the +z side. The detection portion is not limited to being on the bottom surface-side of the channel, and may be on a side surface-side of the channel. For example, when the illumination light enters from the side surface of the channel, sideways-scattered light may be detected from the bottom surface-side of the channel, or sideways-scattered light may be detected from the upper surface-side of the channel. Additionally, the configuration may be such as to detect forward-scattered light. For example, when the illumination light enters from the side surface of the channel, it is possible to detect back-scattered light from the illumination light exit-side of the channel, or to detect forward-scattered light from the illumination light incidence-side of the channel.

Additionally, in the above-described embodiment, a fluid device C including a plurality of lanes 2 arranged in the lengthwise direction (y direction) are indicated as examples, but the plurality of lanes 2 may be arranged in the height direction (z direction). In that case, the solution may be injected from the lengthwise direction (x direction), or may be injected from they direction. There may, for example, be a plurality of irradiation light sources, such that each light source irradiates the microparticles flowing in a lane 2 at a corresponding height. Additionally, the microparticles flowing in the lanes 2 may be irradiated by changing the irradiation direction from at least one irradiation light source.

In the above-mentioned embodiment, in order to adjust the position at which the width of the illumination light L1 is minimized in the z direction, for example, it is possible to adopt a configuration wherein, as a second adjustment portion, a plurality of adjustment portions CL (lenses) having different focal lengths are provided on a turret plate, and the turret plate is rotated so as to position a lens having a desired focal length on the optical path of the illumination light L1, or a configuration wherein a zoom lens is used. Additionally, it is possible to use a plurality of adjustment portions CL having different effective diameters, and to position a lens having a desired effective diameter on the optical path of the illumination light L1, or to use a variable NA diaphragm so as to make the effective diameter of a condensing lens variable. Furthermore, it is possible to use a plurality of expander lenses 22 having different magnifications, and to position expander lenses 22 having desired effective diameters on the optical path of the illumination light L1, or to use a zoom lens so as to make the magnification variable.

Additionally, in the above-described embodiment, the optical axis of the illumination light L1 is parallel to the x axis, but there is no such limitation, and the optical axis may, for example, be tilted by ±10 degrees or ±5 degrees with respect to the x axis, as long as it is in the range of intersection with the above-mentioned orthogonal plane. When the optical axis of the illumination light L1 is parallel to the x axis and is orthogonally incident on the side surface 16*a*, the scattering-angle dependence of Rayleigh-scattered light will theoretically be weakest, but as mentioned above, when Mie-scattered light from the particles larger than the particles that are being measured is eliminated, the noise is reduced, so there is a possibility that the signal intensity of the Rayleigh-scattered light will be higher if the optical axis of the illumination light L1 is tilted with respect to the x axis.

Additionally, in the above-mentioned embodiment, exosomes are used as the particles, but the present device and the present system may be applied to particles other than exosomes. For example, the present device and the present system may be applied not only to organic particles as represented by particles derived from autologous cells such as exosomes (extracellular vesicles) and particles of external origin such as bacteria and viruses, but also to inorganic particles such as metals and silica.

What is claimed is:

1. A particle detection method in which particles in a sample are detected, comprising:
   a mounting step of mounting, on a stage portion, a fluid device comprising a channel through which the particles can move;
   an irradiation step of irradiating the channel with illumination light; and
   a detection step of observing scattered light generated from the particles by irradiation with the illumination light and acquiring image information of the particles,
   wherein in the irradiation step, the illumination light is converged such as to enter the channel by passing through, among side surfaces of the channel, only a first side surface that faces an illumination light incident direction.

2. The particle detection method according to claim 1, wherein
   in the irradiation step, the illumination light is irradiated at a Convergence angle such as to be focused within the first side surface.

3. The particle detection method according to claim 1, wherein
   in the irradiation step, the illumination light is converged such that a width in a direction orthogonal to an optical axis of the illumination light is minimized inside the channel.

4. The particle detection method according to claim 1, wherein
   in the irradiation step, the illumination light is converged such as to exit the channel by passing through, among the side surfaces of the channel, only a second side surface opposite to the first side surface.

5. The particle detection method according to claim 1, wherein
   the channel is formed so as to have a rectangular cross-section, and
   an optical axis of the illumination light is orthogonal to the first side surface.

6. The particle detection method according to claim 1, wherein
   the fluid device comprises an end surface that is positioned closer to a light source of the illumination light than the channel, and
   in the irradiation step, the illumination light is converged such as to enter the fluid device by passing through only the end surface.

7. The particle detection method according to claim 6, wherein
   the fluid device comprises a first substrate and a second substrate, which are laminated and which are formed from materials having refractive indices that are different from each other, and
   the first substrate comprises a groove portion forming the channel, and the end surface.

8. The particle detection method according to claim 1, wherein in the detection step, the scattered light is light scattered sideways by the particles.

9. The particle detection method according to claim 1, comprising
   moving the particles in the channel by electrophoresis.

10. The particle detection method according to claim 1, comprising
    determining information relating to the particles based on the acquired image information.

11. The particle detection method according to claim 10, wherein
    a movement speed and/or a particle size of the particles is determined based on the image information.

12. The particle detection method according to claim 1, wherein
    the particles are exosomes.

13. A particle detection device in which particles in a sample are detected, the particle detection device comprising:
    a stage portion on which is to be mounted a fluid device including a channel into which a sample containing particles can be introduced;
    an irradiation portion configured to irradiate the channel with illumination light;
    an adjustment portion configured to adjust the illumination light; and
    a detection portion configured to observe scattered light generated from the particles in the sample by irradiation with the illumination light and to acquire image information of the particles,
    wherein the adjustment portion adjusts a convergence angle of the illumination light such that an irradiation region on a first side surface of the channel that faces an illumination light incident direction is focused within the first side surface.

14. The particle detection device according to claim 13, wherein
    the adjustment portion adjusts the convergence angle of the illumination light such that a width in a direction orthogonal to an optical axis of the illumination light is minimized inside the channel.

15. The particle detection device according to claim 13, wherein
    the detection portion comprises an acquisition portion configured to acquire image information of the particles; and
    a determination portion configured to determine information relating to the particles based on the image information acquired by the acquisition portion.

16. The particle detection device according to claim 13, comprising
    an application portion configured to apply an electric field in a direction aligned with the channel.

17. The particle detection device according to claim 15, wherein
    the determination portion determines a movement speed and/or a particle size of the particles based on the image information.

18. A particle detection system comprising:
    the fluid device that includes the channel into which the sample containing the particles can be introduced; and
    the particle detection device according to claim 13.

19. A fluid device in use for detecting particles, comprising a first substrate and a second substrate, wherein
    a groove is formed on a lower surface of the first substrate, and the first substrate and the second substrate are bonded together at the lower surface of the first substrate and an upper surface of the second substrate to thereby form the groove into a channel; and
    an end surface of the second substrate, between the upper surface of the second substrate and a lower surface of the second substrate, that faces an illumination light incident direction is positioned further from a light source of the illumination light than an end surface of the first substrate, between an upper surface of the first substrate and the lower surface of the first substrate, that faces the illumination light incident direction.

20. The fluid device according to claim 19, wherein the end surface of the first substrate that faces the illumination light incident direction is mirror-finished.

21. The particle detection method according to claim 1, wherein a size of a particle as an object of detection is about 30 to 100 nm in diameter.

* * * * *